United States Patent
Hsu et al.

(10) Patent No.: US 7,621,173 B2
(45) Date of Patent: Nov. 24, 2009

(54) NANO-IDENTATION ULTRASONIC DETECTING SYSTEM AND METHOD THEREOF

(75) Inventors: Jiong-Shiun Hsu, Taichung (TW); Kai-Yu Cheng, Taipei (TW); Yu-Shyan Liu, Taipei County (TW); Jeah-Sheng Wu, Hsinchu (TW); Yu-Yi Su, Hualien County (TW); Chi-Sheng Chang, Taoyuan County (TW)

(73) Assignee: Industrial Technology Research Institute, Hsinchu (TW)

( * ) Notice: Subject to any disclaimer, the term of this patent is extended or adjusted under 35 U.S.C. 154(b) by 378 days.

(21) Appl. No.: 11/552,118

(22) Filed: Oct. 23, 2006

(65) Prior Publication Data
US 2007/0151340 A1 Jul. 5, 2007

(30) Foreign Application Priority Data
Dec. 30, 2005 (TW) .............................. 94147870 A

(51) Int. Cl.
*G01N 3/42* (2006.01)
(52) U.S. Cl. .............................................. 73/81; 73/82
(58) Field of Classification Search ............... 73/81–85, 73/620, 624–625, 629, 790, 794–795, 799, 73/806–808, 813, 821
See application file for complete search history.

(56) References Cited

U.S. PATENT DOCUMENTS

| | | | | |
|---|---|---|---|---|
| 4,270,388 | A * | 6/1981 | Eggleton | 73/603 |
| 4,771,792 | A * | 9/1988 | Seale | 600/587 |
| 4,852,397 | A * | 8/1989 | Haggag | 73/82 |
| 6,134,954 | A * | 10/2000 | Suresh et al. | 73/81 |
| 6,289,734 | B1 * | 9/2001 | Daugela | 73/573 |
| 6,494,840 | B1 * | 12/2002 | Mak et al. | 600/446 |
| 6,569,098 | B2 * | 5/2003 | Kawchuk | 600/437 |
| 7,165,463 | B2 * | 1/2007 | Liu et al. | 73/861 |

* cited by examiner

*Primary Examiner*—Helen C. Kwok
(74) *Attorney, Agent, or Firm*—Quintero Law Office

(57) ABSTRACT

A nano-indentation ultrasonic detecting system for detecting mechanical properties of a target material. An indentation device, disposed on a surface of the target material, generates an indentation on the surface, obtaining the relation between the Young's modulus and the Poisson's ratio of the target material. An ultrasonic generator is movably disposed on the surface of the target material, generating at least two different ultrasonic signals thereon. An ultrasonic receiver is disposed on the surface of the target material and separated from the ultrasonic generator, receiving the ultrasonic signals. The result of a nano-indentation experiment are applied in the ultrasonic theory and iterated by the ultrasonic experimental data and theory, obtaining the Young's modulus of the target material. The obtained Young's modulus of the target material is substituted back in the result of the nano-indentation experiment, obtaining the Poisson's ratio of the target material.

10 Claims, 6 Drawing Sheets

NANO-IDENTATION ULTRASONIC DETECTING SYSTEM AND METHOD THEREOF

BACKGROUND OF THE INVENTION

1. Field of the Invention

The invention relates to a nano-indentation ultrasonic detection system and method thereof and in particular to a nano-indentation ultrasonic detecting system and method thereof precisely detecting Young's modulus and Poisson's ratio for a material.

2. Description of the Related Art

A conventional nano-indentation system performs indentation experiments on a surface of a material. Information of load and displacement during the indentation experiments are recorded. Mechanical properties, such as indentation hardness and reduced modulus, of the material can thus be obtained. Moreover, by setting the appropriate conditions, other properties, such as adhesion, fracture mechanics, tribology, and fatigue, of the material can also be obtained. Nevertheless, the reduced modulus obtained by the conventional nano-indentation system is a relationship between Young's modulus and Poisson's ratio of the material. The Young's modulus can be determined only by speculating the Poisson's ratio in advance. Accordingly, when the speculated Poisson's ratio differs from the real Poisson's ratio of the material, especially for the thin film for which the Poisson's ratio cannot be detected by conventional experimental approaches, the determined Young's modulus is rendered incorrect.

FIG. 1 is a schematic geometric view of an indenter 10 of a conventional nano-indentation system indenting a surface 21 of a material 20. $h_{max}$ denotes the maximum indented displacement of the surface 21, generated by the indenter 10. $h_c$ denotes the contact depth between the indenter 10 and the surface 21. $h_s$ denotes the vertical distance between an initial contact position of the indenter 10 and surface 21 and the initial position of the surface 21 being not indented. $h_r$ denotes the residual depth of the surface 21. The $h_{max}$, $h_c$, and $h_s$ form as:

$$h_{max} = h_c + h_s$$

FIG. 2 is a diagram showing the relation between the load (P) of the indenter and the displacement (h) of the surface of the material according to FIG. 1. $P_{max}$ denotes the magnitude of the load of the indenter 10 at $h_{max}$ (the maximum indented displacement of the surface 21), a denotes a loading curve of the indenter 10, and b denotes an unloading curve of the indenter 10. Moreover, the unloading curve b can be expressed by an equation as follows:

$$P = K(h - h_r)^m,$$

wherein K and m are fitted constants from data of unloading experiments.

Moreover, contact stiffness s is the slope of the unloading curve b at $h_{max}$ and can be expressed as:

$$S = \frac{dP}{dh}\bigg|_{h = h_{max}}$$

According to contact mechanics, the reduced modulus ($E_r$) of the indenter 10 and material 20 and a tip area function of an indentation can be expressed as:

$$E_r = \frac{\pi}{2}\frac{S}{\sqrt{A}},$$

wherein A denotes the cross-sectional area of the initial contact position between the indenter 10 and the surface 21.

Additionally, the reduced modulus ($E_r$) can be expressed as:

$$\frac{1}{E_r} = \frac{1 - v_1^2}{E_1} + \frac{1 - v_2^2}{E_2},$$

wherein $E_1$ and $E_2$ respectively denote the Young's moduli of the indenter 10 and material 20, and $v_1$ and $v_2$ respectively denote the Poisson's ratios thereof.

As depth of an indentation produced by the nano-indentation system is often shallow, precise tip area function of the indentation must be obtained. Oliver and Pharr performed multiple indentation experiments on fused silica and thereby fit the following tip area function according to the data thereof:

$$A(h_c) = C_0 h_c^2 + C_1 h_c^1 + C_2 h_c^{1/2} + C_3 h_c^{1/4} + \ldots + C_8 h_c^{1/128},$$

wherein $C_0$ is the coefficient of the indenter with a perfect geometric shape and $C_1$ to $C_8$ are fitted constants.

Moreover, contact mechanics provides the following formula:

$$h_s = \varepsilon \frac{P_{max}}{S},$$

wherein $\varepsilon$ is a constant related to the geometric shape of the indenter 10. For example, the $\varepsilon$ of the indenter of Berkovich is 0.75. Accordingly, as the material of the indenter 10 is known, the reduced modulus of the indenter 10 and material 20 can be determined by the aforementioned formulae. Nevertheless, the conventional nano-indentation system can only obtain the relation between the Young's modulus and the Poisson's ratio of the material, rather than the respective Young's modulus and Poisson's ratio thereof.

Hence, there is a need for a nano-indentation ultrasonic detecting system and method overcoming the disadvantage of the conventional nano-indentation system detecting the Young's modulus of a material by speculating the Poisson's ratio thereof in advance and avoid obtaining inaccurate Young's modulus thereof.

BRIEF SUMMARY OF THE INVENTION

A detailed description is given in the following embodiments with reference to the accompanying drawings.

An exemplary embodiment of the invention provides a nano-indentation ultrasonic detecting system for detecting mechanical properties of a target material. The nano-indentation ultrasonic detecting system comprises a nano-indentation device, an ultrasonic generator, and an ultrasonic receiver. The nano-indentation device is disposed on a surface of the target material. The nano-indentation device generates an indentation on the surface, obtaining the relation between the Young's modulus and the Poisson's ratio of the target material. The ultrasonic generator is movably disposed on the surface of the target material, generating at least two different ultrasonic signals thereon. The ultrasonic receiver is disposed on the surface of the target material and separated from the ultrasonic generator, receiving the ultrasonic signals. The results of a nano-indentation experiment are applied in the ultrasonic theory and iterated by the ultrasonic experiment and theory, obtaining the Young's modulus of the target material. The obtained Young's modulus of the target material is then substituted back in the result of the nano-indentation experiment, obtaining the Poisson's ratio of the target material.

Another exemplary embodiment of the invention provides a nano-indentation ultrasonic detecting method for detecting mechanical properties of a target material. The nano-indentation ultrasonic detecting method comprises generating at least two different ultrasonic signals on a surface of the target material by an ultrasonic generator, receiving the ultrasonic signals by an ultrasonic receiver, analyzing the ultrasonic signals, obtaining an phase-velocity value thereof, performing an indentation experiment on the surface of the target material by an indentation device, obtaining a formula related to the Young's modulus and Poisson's ratio of the target material, resolving the formula related to the Young's modulus and Poisson's ratio of the target material by wave mechanics theory, obtaining the wave mechanics theory containing only the related Young's modulus, numerically iterating the experimental and theoretical phase-velocity values of the ultrasonic signals; repeatedly speculating about the Young's modulus of the target material until converges, obtaining the obtained Young's modulus thereof, and applying the obtained Young's modulus in the formula related to the Young's modulus and Poisson's ratio of the target material, obtaining the real Poisson's ratio thereof.

In order to make the aforementioned and other objects, features and advantages of the present invention comprehensible, a preferred embodiment accompanied with figures is described in detail below.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
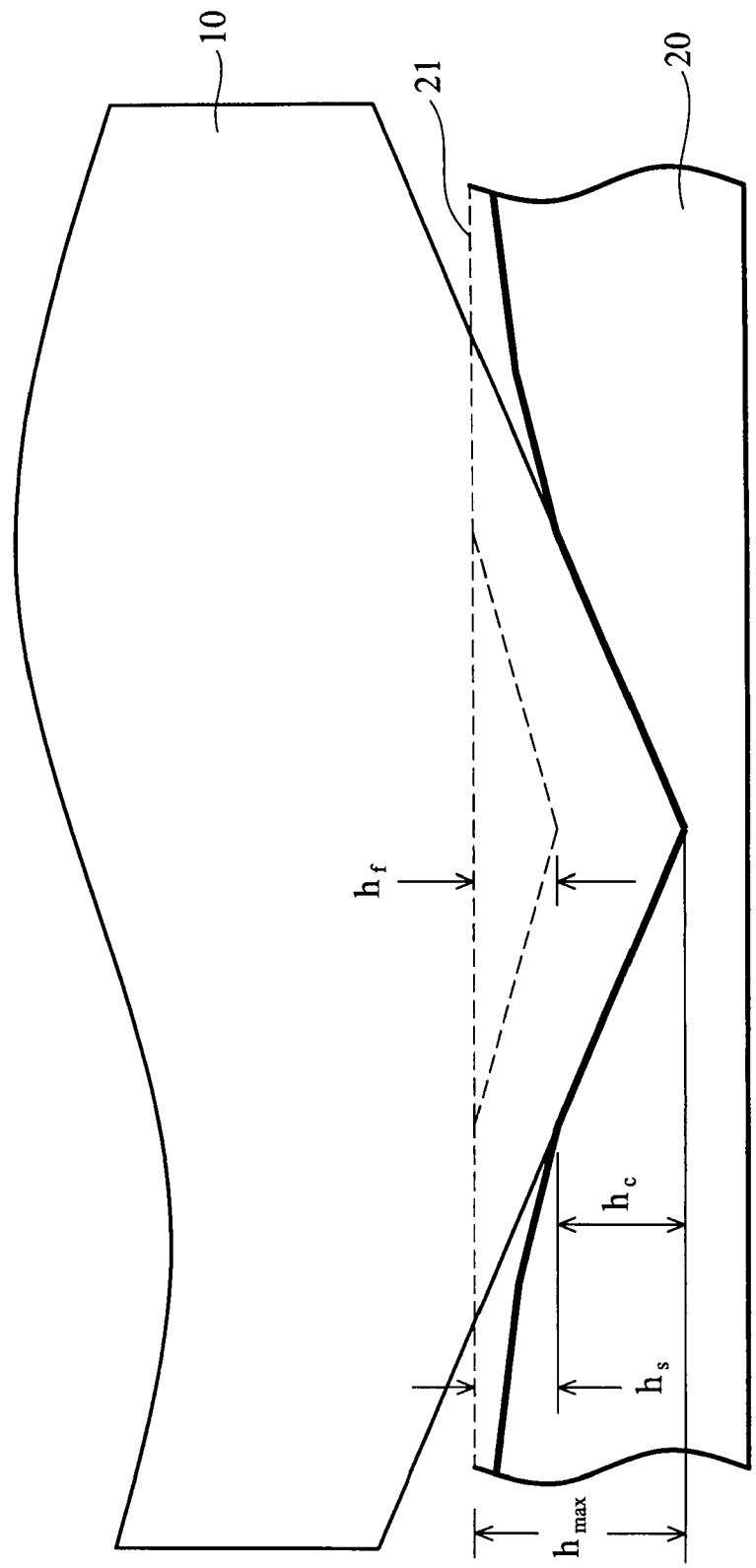
FIG. 1 is a schematic geometric view of an indenter of a conventional nano-indentation system indenting a surface of a material.
Figure 2:
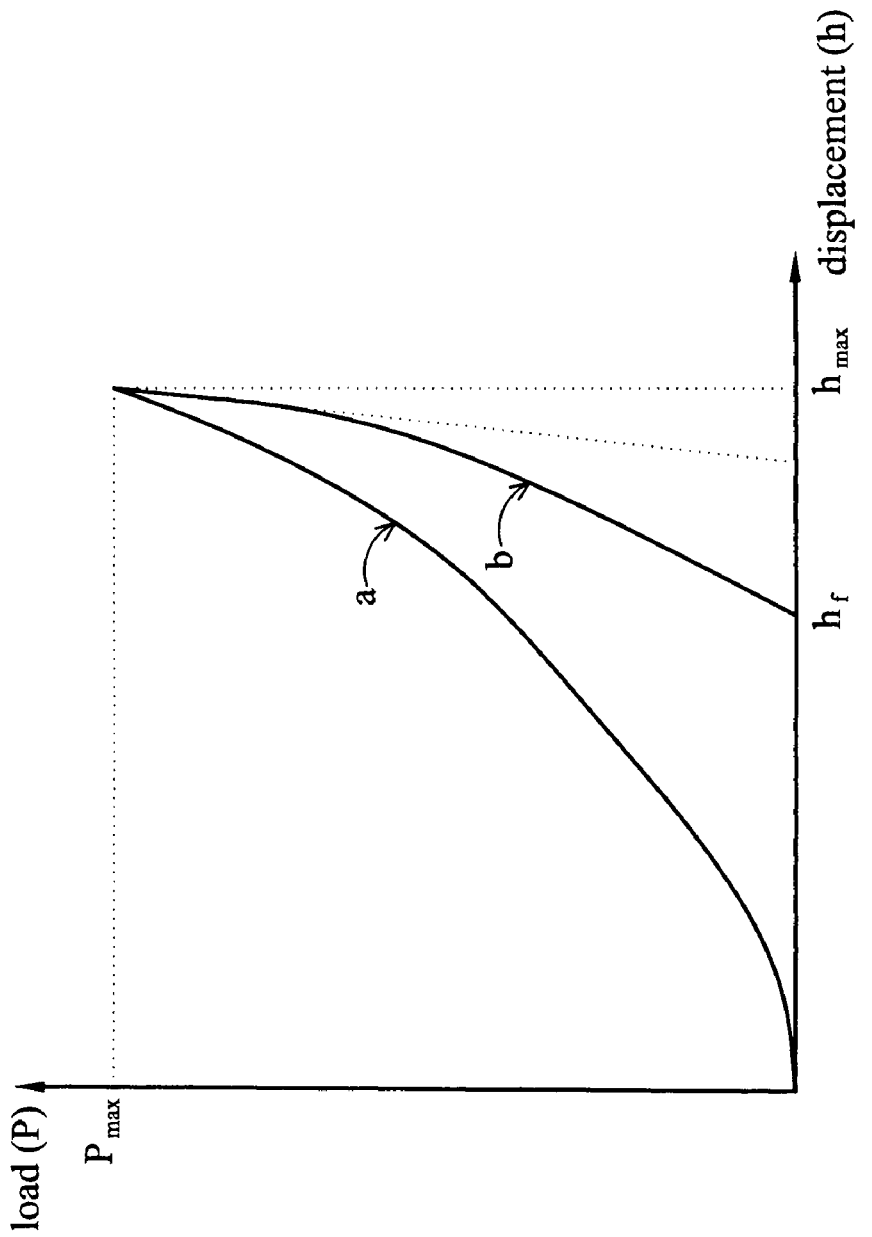
FIG. 2 is a diagram showing the relation between the load of the indenter and the displacement of the surface of the material according to FIG. 1.
Figure 3:
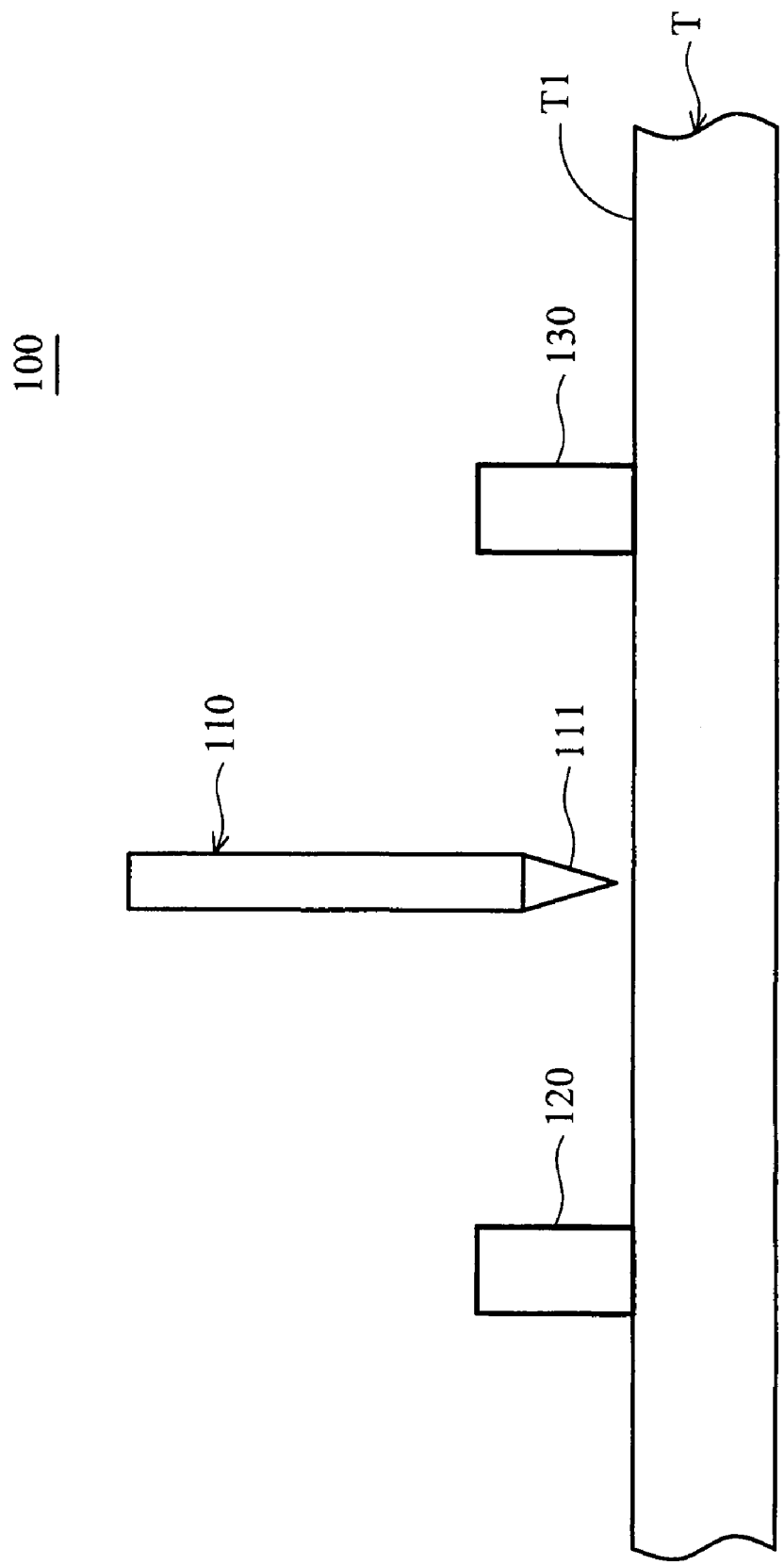
FIG. 3 is a schematic view of a nano-indentation ultrasonic detecting system of the invention.

Referring to FIG. 3, the nano-indentation ultrasonic detecting system 100 for detecting mechanical properties (such as Young's modulus and Poisson's ratio) of a target material T comprises an indentation device 110, an ultrasonic generator 120, and an ultrasonic receiver 130.

The indentation device 110 comprises an indenter 111 and is disposed on a surface T1 of the target material T, generating an indentation thereon, obtaining a formula related to the Young's modulus and Poisson's ratio of the target material T.

The ultrasonic generator 120 is movably disposed on the surface T1 of the target material T, generating two different ultrasonic signals thereon. Namely, the ultrasonic generator 120 generates two ultrasonic signals at two different positions on the surface T1.

Figure 4B:
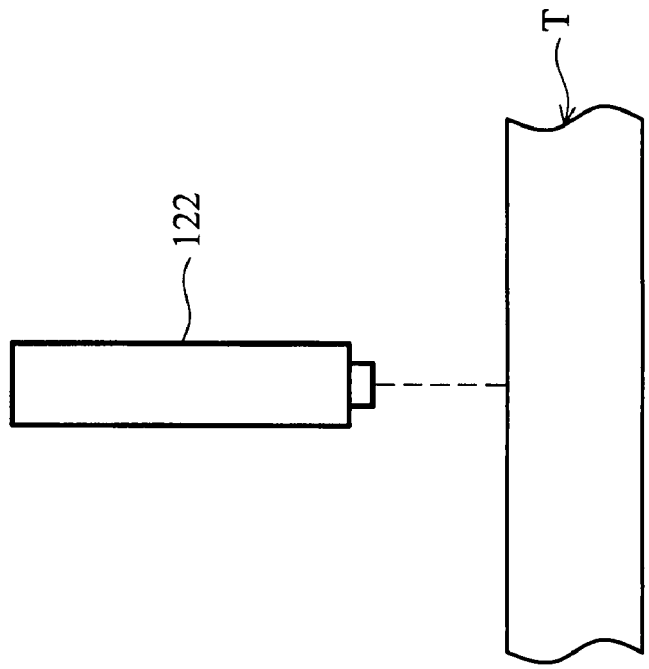
FIG. 4B is a schematic view of a pulse laser source of an ultrasonic generator of the nano-indentation ultrasonic detecting system of the invention.
Figure 4A:
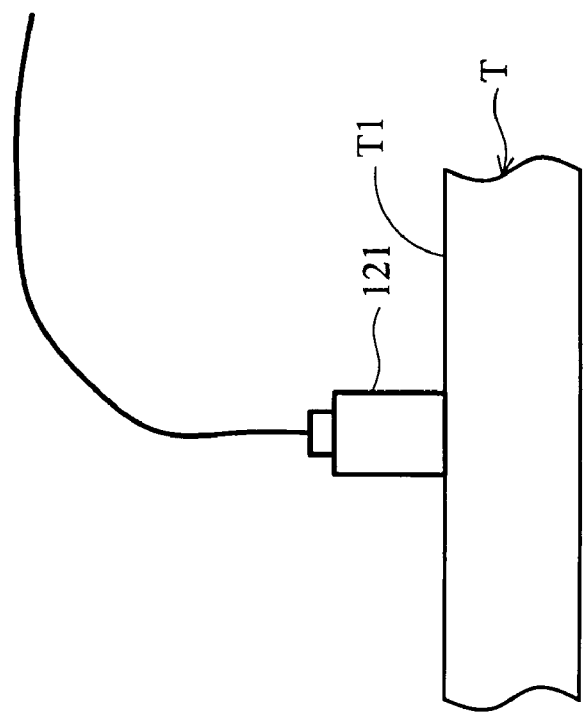
FIG. 4A is a schematic view of a contact ultrasonic transmitter of an ultrasonic generator of the nano-indentation ultrasonic detecting system of the invention.

Additionally, as shown in FIG. 4A, the ultrasonic generator 120 may comprise a contact ultrasonic transmitter 121 disposed on the surface T1 of the target material T.

Alternatively, as shown in FIG. 4B, the ultrasonic generator 120 may comprise a pulse laser emitter 122 separated from the surface T1 of the target material T by a distance, generating ultrasonic signals thereon.

As shown in FIG. 3, the ultrasonic receiver 130 is disposed on the surface T1 of the target material T and separated from the ultrasonic generator 120, receiving the ultrasonic signals transmitted by the surface T1. A formula related to the Young's modulus and Poisson's ratio of the target material T can be obtained by analyzing the ultrasonic signals received by the ultrasonic receiver 130. The formula related to the Young's modulus and Poisson's ratio and obtained by the indentation device 110 is applied in the formula obtained by analyzing the ultrasonic signals received by the ultrasonic receiver 130. An ultrasonic theory containing only the Young's modulus of the target material T can be obtained. The Young's modulus of the target material T can be determined by iteration of the ultrasonic experiment and theory. The obtained Young's modulus is applied in the results of the nano-indentation experiment. The Poisson's ratio of the target material T is then obtained.

Figure 5B:
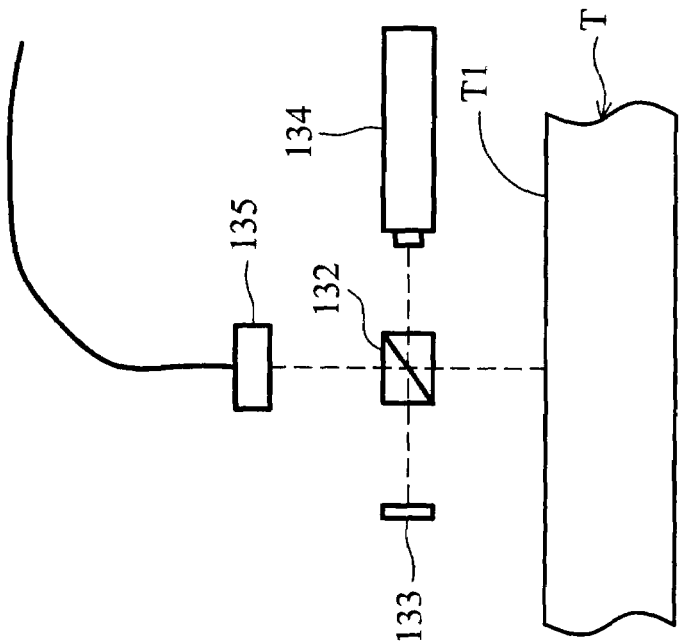
FIG. 5B is a schematic view of a beam splitter, a reflective mirror, a light emitter, and a detector of an ultrasonic receiver of the nano-indentation ultrasonic detecting system of the invention.
Figure 5A:
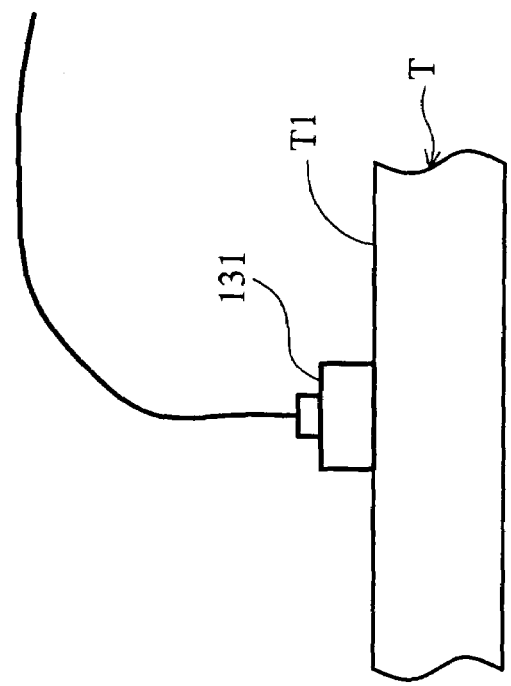
FIG. 5A is a schematic view of a contact ultrasonic detector of an ultrasonic receiver of the nano-indentation ultrasonic detecting system of the invention.

Additionally, as shown in FIG. 5A, the ultrasonic receiver 130 may comprise a contact ultrasonic detector 131 disposed on the surface T1 of the target material T.

Alternatively, as shown in FIG. 5B, the ultrasonic receiver 130 may comprise a beam splitter 132, a reflective mirror 133, a light emitter 134, and a detector 135. The beam splitter 132 is separated from the surface T1 of the target material T by a distance. The reflective mirror 133, the light emitter 134, and the detector 135 are adjacent to the beam splitter 132. The beam splitter 132 is disposed between the reflective mirror 133 and the light emitter 134 and between the detector 135 and the surface T1 of the target material T. Accordingly, the light emitter 134 outputs laser to the reflective mirror 133 and the surface T1 of the target material T through the beam splitter 132. The detector 135 receives laser reflected by the surface T1 and the reflective mirror 133 when the ultrasonic signals are transmitted under the beam splitter 132.

The following description is directed to a method for obtaining the Young's modulus and Poisson's ratio of the target material T using the nano-indentation ultrasonic detecting system 100.

The ultrasonic generator 120 generates or arouses two ultrasonic signals at two different positions ($x_1$ and $x_2$) on the surface T1 of the target material T. The ultrasonic receiver 130 receives the ultrasonic signals ($I_1(t)$ and $I_2(t)$) aroused at the positions ($x_1$ and $x_2$). The ultrasonic signals ($\phi_1(\omega)$ and $\phi_2(\omega)$) are then converted into two frequency domain signals ($\phi_1(\omega)$ and $\phi_2(\omega)$) using fast Fourier transform (FFT). The frequency domain signals ($\phi_1(\omega)$ and $\phi_2(\omega)$) are calculated, obtaining an experimental phase velocity ($\overline{C}_p(\omega)$). The experimental phase velocity ($\overline{C}_p(\omega)$), positions ($x_1$ and $x_2$), angular frequency ($\omega$), and phase ($\phi_1(\omega)$ and $\phi_2(\omega)$) form a formula of experimental phase-dispersion velocity as follows:

$$\overline{C}_p(\omega) = \frac{|x_1 - x_2|\omega}{\phi_1(\omega) - \phi_2(\omega)}$$

In another aspect, the indentation device 110 performs an indentation experiment on the surface T1 of the target material T. Data of load (P) and displacement (h) of the indenter 111 are recorded during the indentation experiment. Specifically, the material properties, such as the Young's modulus and Poisson's ratio, of the indenter 111 is known, and the cross-sectional area (A) of the initial contact position between the indenter 111 and the surface T1 and maximum indented displacement (h) of the indenter 111 or surface T1 can be directly measured by an optical method or scanning microscopy. Alternatively, the cross-sectional area (A) and maximum indented displacement (h) can be obtained by applying multiple loads on the surface T1 of the target material T and fitting a function with a tip area function. The aforementioned indentation experiment obtains the reduced modulus ($E_r$) of the indenter 111 and target material T. The reduced modulus ($E_r$) can be expressed as:

$$\frac{1}{E_r} = \frac{1-v_1^2}{E_1} + \frac{1-v_2^2}{E_2},$$

wherein $E_1$ and $E_2$ respectively denote the Young's moduli of the indenter 111 and target material T, and $v_1$ and $v_2$ respectively denote the Poisson's ratios thereof. Accordingly, $E_1$ and $v_1$ of the indenter 111 are known.

In another aspect, the formula $$\left(\frac{1}{E_r} = \frac{1-v_1^2}{E_1} + \frac{1-v_2^2}{E_2}\right)$$

obtained from the indentation device 110 is solved with a formula ($C_p(\omega)$) of theoretical phase-velocity dispersion obtained by wave mechanics theory. The Young's modulus ($E_2$) of the target material T is speculated, defining a function Y as follows:

$$Y = \sum_{j=1}^{n} \left[(C_p)_j - (\overline{C}_p)_j\right]^2.$$

Accordingly, the Young's modulus ($E_2$) of the target material T is repeatedly speculated and numerically iterated (such as using a least squares method) until the function Y converges. When the function Y converges, the speculated Young's modulus matches the real Young's modulus of the target material T. The real Young's modulus ($E_2$) of the target material T can then be substituted into the formula $$\frac{1}{E_r} = \frac{1-v_1^2}{E_1} + \frac{1-v_2^2}{E_2},$$

thus obtaining the real Poisson's ratio ($v_2$) thereof.

Figure 6:
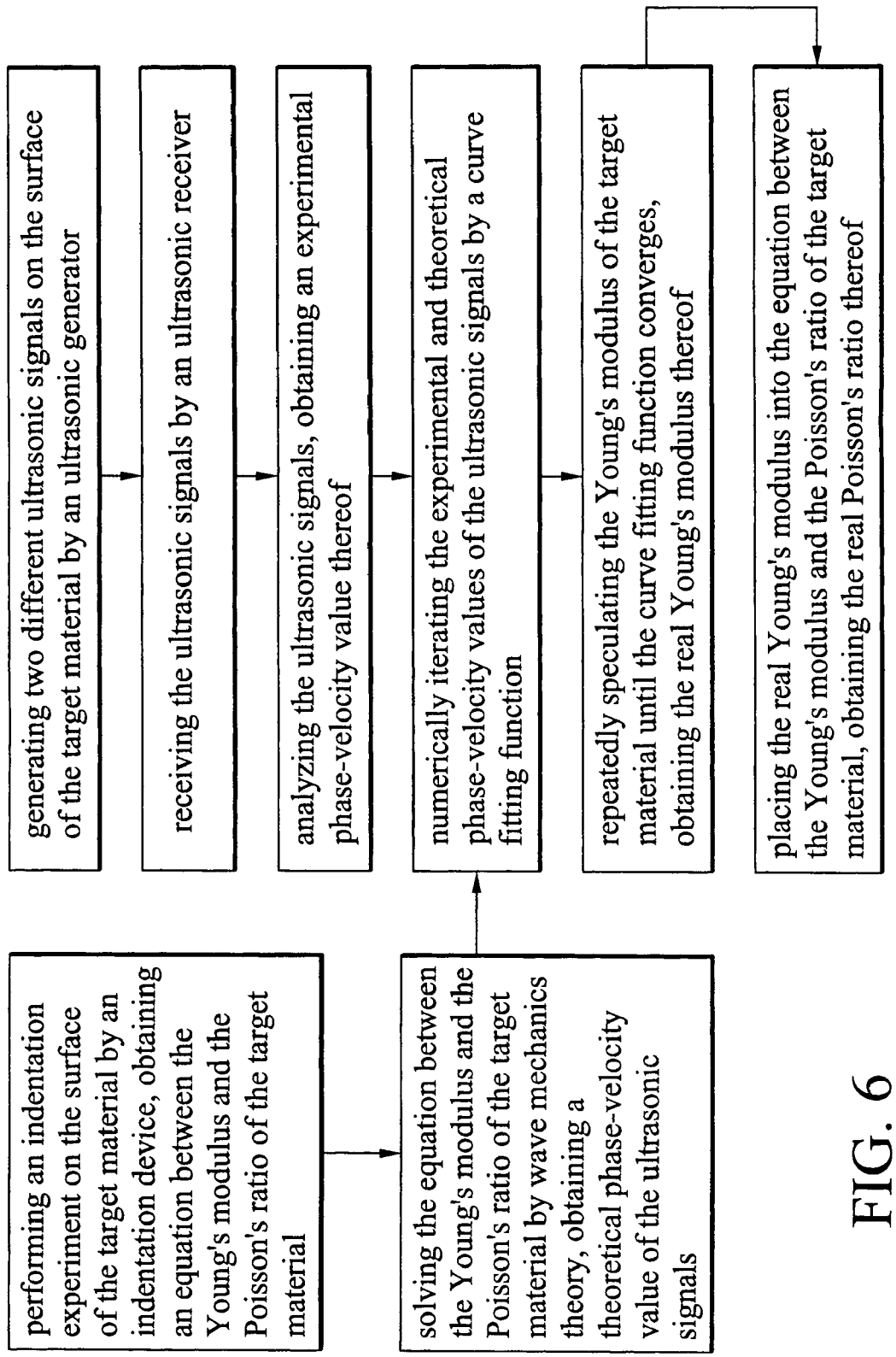
FIG. 6 is a flowchart of a nano-indentation ultrasonic detecting method of the invention.

A flowchart of the aforementioned nano-indentation ultrasonic detecting method is shown in FIG. 6.

In conclusion, the disclosed nano-indentation ultrasonic detecting system and method can overcome the disadvantage of the conventional nano-indentation system for detecting the mechanical property of a material. Specifically, in the disclosed nano-indentation ultrasonic detecting system and method, the Young's modulus and Poisson's ratio of the material can be obtained without speculation of the Poisson's ratio thereof in advance.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A nano-indentation ultrasonic detecting system for detecting mechanical properties of a target material, comprising:

an indentation device disposed on a surface of the target material, wherein the indentation device generates an indentation on the surface, obtaining a relationship between a Young's modulus and a Poisson's ratio of the target material;

an ultrasonic generator movably disposed on the surface of the target material, comprising a pulse laser emitter separated from the surface of the target material to generate at least two different ultrasonic signals thereon; and an ultrasonic receiver disposed on the surface of the target material and separated from the ultrasonic generator for receiving the ultrasonic signals, comprising a beam splitter, a reflective mirror, a light emitter and a detector, wherein the beam splitter is separated from the surface of the target material, the reflective mirror, the light emitter and the detector are adjacent to the beam splitter, the beam splitter is disposed between the reflective mirror and the light emitter and between the detector and the surface of the target material, and the beam splitter is arranged such that a laser outputting from the light emitter and passing through the beam splitter is directly received by the reflective mirror without passing through the surface of the target material;

wherein the Young's modulus of the target material is obtained by analyzing the ultrasonic signals received by the ultrasonic receiver, and the Poisson's ratio of the target material is determined from the obtained Young's modulus and the relationship provided from a nano-indentation experiment.

2. The nano-indentation ultrasonic detecting system as claimed in claim 1, wherein the ultrasonic generator comprises a contact ultrasonic transmitter disposed on the surface of the target material.

3. The nano-indentation ultrasonic detecting system as claimed in claim 1, wherein the ultrasonic receiver comprises a contact ultrasonic detector disposed on the surface of the target material.

4. A nano-indentation ultrasonic detecting method for detecting mechanical properties of a target material, comprising:

generating at least two different ultrasonic signals on a surface of the target material by an ultrasonic generator, wherein the ultrasonic generator comprises a pulse laser emitter separated from the surface of the target material to generate the at least two different ultrasonic signals thereon;

receiving the ultrasonic signals by an ultrasonic receiver, wherein the ultrasonic receiver comprises a beam splitter, a reflective mirror, a light emitter and a detector, wherein the beam splitter is separated from the surface of the target material, the reflective mirror, the light emitter and the detector are adjacent to the beam splitter, and the beam splitter is disposed between the reflective mirror and the light emitter between the detector and the surface of the target material, and a laser outputting from the light emitter and passing through the beam splitter is directly received by the reflective mirror without passing through the surface of the target material;

analyzing the ultrasonic signals, obtaining an experimental phase-velocity value thereof;

performing an indentation experiment on the surface of the target material by an indentation device, obtaining a formula related to a Young's modulus and a Poisson's ratio of the target material;

resolving the formula related to the Young's modulus and the Poisson's ratio of the target material using wave mechanics theory, obtaining a theoretical phase-velocity value of the ultrasonic signals;

numerically iterating the experimental and theoretical phase-velocity values of the ultrasonic signals;

repeatedly speculating about the Young's modulus of the target material until converges, obtaining the Young's modulus thereof; and substituting the Young's modulus into the formula related to the Young's modulus and the Poisson's ratio of the target material, obtaining the Poisson's ratio of the target material.

5. The nano-indentation ultrasonic detecting method as claimed in claim 4, further comprising converting the ultrasonic signals into two frequency domain signals using fast Fourier transform and calculating the frequency domain signals, obtaining the experimental phase-velocity value of the ultrasonic signals.

6. The nano-indentation ultrasonic detecting method as claimed in claim 4, wherein the indentation device is disposed on the surface of the target material, generating an indentation thereon.

7. The nano-indentation ultrasonic detecting method as claimed in claim 4, wherein the ultrasonic generator is movably disposed on the surface of the target material.

8. The nano-indentation ultrasonic detecting method as claimed in claim 7, wherein the ultrasonic generator comprises a contact ultrasonic transmitter disposed on the surface of the target material.

9. The nano-indentation ultrasonic detecting method as claimed in claim 4, wherein the ultrasonic receiver is disposed on the surface of the target material and separated from the ultrasonic generator.

10. The nano-indentation ultrasonic detecting method as claimed in claim 9, wherein the ultrasonic receiver comprises a contact ultrasonic detector disposed on the surface of the target material.

* * * * *

UNITED STATES PATENT AND TRADEMARK OFFICE
CERTIFICATE OF CORRECTION

PATENT NO. : 7,621,173 B2  Page 1 of 1
APPLICATION NO. : 11/552118
DATED : November 24, 2009
INVENTOR(S) : Jiong-Shiun Hsu et al.

It is certified that error appears in the above-identified patent and that said Letters Patent is hereby corrected as shown below:

on the title page, (54), the title, and column 1 line 1 should read:

NANO-INDENTATION ULTRASONIC DETECTING SYSTEM AND METHOD THEREOF

Signed and Sealed this

Thirtieth Day of March, 2010

David J. Kappos
*Director of the United States Patent and Trademark Office*

UNITED STATES PATENT AND TRADEMARK OFFICE
CERTIFICATE OF CORRECTION

PATENT NO.       : 7,621,173 B2                                          Page 1 of 1
APPLICATION NO. : 11/552118
DATED            : November 24, 2009
INVENTOR(S)      : Hsu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 410 days.

Signed and Sealed this

Twenty-sixth Day of October, 2010

David J. Kappos
*Director of the United States Patent and Trademark Office*